(12) United States Patent
Katz

(10) Patent No.: US 7,129,713 B2
(45) Date of Patent: Oct. 31, 2006

(54) CAPACITIVE MOISTURE SENSOR

(75) Inventor: Bernard Roy Katz, Rockaway, NJ (US)

(73) Assignee: Delmhorst Instrument Co., Towaco, NJ (US)

( * ) Notice: Subject to any disclaimer, the term of this patent is extended or adjusted under 35 U.S.C. 154(b) by 22 days.

(21) Appl. No.: 10/761,841

(22) Filed: Jan. 21, 2004

(65) Prior Publication Data

US 2005/0156608 A1 Jul. 21, 2005

(51) Int. Cl.
*G01R 27/26* (2006.01)

(52) U.S. Cl. ............... 324/664; 324/658; 324/686; 324/689

(58) Field of Classification Search ............... 324/658, 324/686, 664–666, 689
See application file for complete search history.

(56) References Cited

U.S. PATENT DOCUMENTS

| | | | | |
|---|---|---|---|---|
| 3,771,548 A | * | 11/1973 | Rauchwerger | 137/392 |
| 4,259,632 A | * | 3/1981 | Ahtiainen | 324/664 |
| 4,620,141 A | * | 10/1986 | McCumber et al. | 318/483 |
| 4,823,600 A | * | 4/1989 | Biegel et al. | 73/592 |
| 4,845,421 A | * | 7/1989 | Howarth et al. | 324/688 |
| 4,966,158 A | * | 10/1990 | Honma et al. | 600/547 |
| 5,479,104 A | * | 12/1995 | Cambell | 324/690 |
| 5,486,815 A | * | 1/1996 | Wagner | 340/602 |
| 5,859,536 A | * | 1/1999 | Stockton | 324/664 |
| 2003/0169054 A1 | * | 9/2003 | Rynhart et al. | 324/649 |

* cited by examiner

*Primary Examiner*—Anjan Deb
*Assistant Examiner*—Marina Kramskaya
(74) *Attorney, Agent, or Firm*—Notaro & Michalos P.C.

(57) ABSTRACT

A moisture sensing apparatus includes an oscillator for supplying an AC signal to a driven ring of a sensor having a pad inside the ring, and a ground plate around the ring. An amplifier forms part of a temperature-compensated, precision rectifier, and is connected to the pad. A first diode connected to the output of the amplifier in a feedback loop of the amplifier, where the amplifier nullifies temperature variation effects upon the diode, and supplies a rectified signal which is a function of moisture content of material in contact with the sensor. A second diodes is connected between the amplifier output and other input of the amplifier. The sensor has a rounded configuration to avoid electrostatic field fringing effects, and a passive impedance with both resistive and capacitive members is connected in parallel with the sensor to provide a functional baseline for the rectified signal.

15 Claims, 3 Drawing Sheets

CAPACITIVE MOISTURE SENSOR

FIELD AND BACKGROUND OF THE INVENTION

The present invention relates generally to the field of moisture detectors, and, in particular, to a novel mechanism and method of signal processing for sensing of moisture in building construction materials, including wood, concrete, gypsum, roofing felt, various flooring and other materials.

Although the approach illustrated is intended for use in moisture sensing by surface contact with a measurement sample, this is the preferred embodiment for the invention, with variations possible in sensor shape and configuration, and electronic circuitry described herein, known to those skilled in the art to be considered as integral to the spirit and scope of this disclosure.

It is an object of this disclosure to illustrate novelty of the design approach and reading stability offered by the same.

Many approaches to capacitive moisture measurement have been utilized over a substantial number of years.

Virtually all rely upon creation of an electrostatic field within the sample undergoing moisture measurement, where the alternating current potential component between two electrodes within the field is measured. Such an arrangement is described in U.S. Pat. No. 3,967,197.

Alternatively, some designs utilize a three electrode configuration, where a form of voltage division occurs between a driven and common or ground electrode, and a receiving electrode via the induced electrostatic field. Often this alternative geometry is implemented in the form of a center receiving electrode, surrounded by a co-planar driven or transmitting ring, in turn surrounded by a coplanar ground plane surface. Such an arrangement is described in U.S. Pat. No. 5,486,815, which specifically utilizes a rectangular arrangement of the stated three electrode implementation. Other approaches use a multiplicity of electrodes for specific measurement purposes.

Electronic circuitry for sensor excitation and reading of sensor output generally consists of an oscillator for excitation, and a diode detector for development of a DC voltage related to peak, average, or other parameter which relates the AC component to a DC value required for display purposes, be the display analog or digital. Commonly the diode detector is temperature compensated to an extent in order to minimize accuracy degradation due to the well known phenomenon of diode voltage drop dependence upon temperature. In silicon diodes, this effect is approximately −2.2 millivolts per degree Celsius. In virtually all instances, another diode or PN junction of a bipolar transistor is used for compensation, but due to circuit design constraints, it cannot be employed in such a way that the current versus time profile is exactly the same as the measurement rectification diode.

While the subject profile in each of the diodes or other PN junction devices can be quite similar, the profiles cannot be exactly the same, or no way will exist for extraction of a DC signal from the receiving electrode of the sensor. Dissimilarities between diode current profiles, while small, become meaningful due to the need for implementing temperature compensation involving very small signals. In some instances of instrument operation, there are differences of only several millivolts in sensor signal output when sensing moisture content of certain relatively dry materials. Under such conditions, temperature of the measurement instrument may meaningfully influence moisture reading accuracy. Indeed, some design approaches totally ignore the degrading effects of diode temperature. One example is found in U.S. Pat. No. 4,733,166, where a diode 82 in FIG. 4 thereof, serves as an RF amplitude detector, but is not voltage drop or temperature compensated.

A need remains for an improved moisture detector, particularly one with improved temperature independence and improved moisture signal sensitivity.

SUMMARY OF THE INVENTION

It is an object of the present invention to provide new and useful features which may be utilized individually or in combination, for the design and fabrication of a capacitance balanced moisture sensing apparatus which exhibits superior characteristics regarding reading stability, and particularly but not exclusively, regarding performance under conditions of differing temperatures.

Accordingly, another object of the invention is to provide a moisture sensing apparatus which comprises an oscillator with an output for supplying an AC signal and an operational amplifier with rectifier means for supplying a rectified signal that is proportional to a moisture content of material that is in contact with a contact plane of the contact sensor, the contact sensor comprising means defining an support substrate, a conductive sensor pad on the support substrate, a conductive driven ring on the support substrate, extending around the pad and spaced from the pad to define a first closed loop around the pad and a conductive ground plate on the support substrate, extending around the ring and defining a second closed loop around the ring, the pad, the ring and the plate all lying in the contact plane for the sensor, which contact plane is adapted to be in contact with a surface for measuring moisture content at the surface, as a function of capacitance across the loops, the pad, the ring, the plate, and the loops having no angular corners so as to minimize electrostatic field fringing effects.

Another object of the invention is to provide a moisture sensing apparatus comprising an oscillator having an output for supplying an AC signal, a contact sensor connected to the oscillator for changing the AC signal as a function of moisture content at a surface in contact with the contact sensor, a precision rectifier connected to the sensor for rectifying a signal from the sensor to form a DC signal that is proportional the moisture content and a reactive impedance connected across the sensor for providing a baseline signal for DC signal.

A still further object of the invention is to provide a moisture sensing apparatus comprising an oscillator having an output for supplying an AC signal, a sensor having a sensor pad, a driven ring around the pad and connected to the oscillator output, and a ground plate around the ring, an operational amplifier having one input connected to the pad, another input, and an output, a first diode connected to the output of the operational amplifier in a feedback loop between the operational amplifier output and the other input of the operational amplifier to compensate for variations in the rectified signal that are due to temperature variations of the diode, the first diode having an output for supplying a rectified signal that is proportional to a moisture content of material that is in contact with the sensor and a second diode connected between the output and other input of the amplifier.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
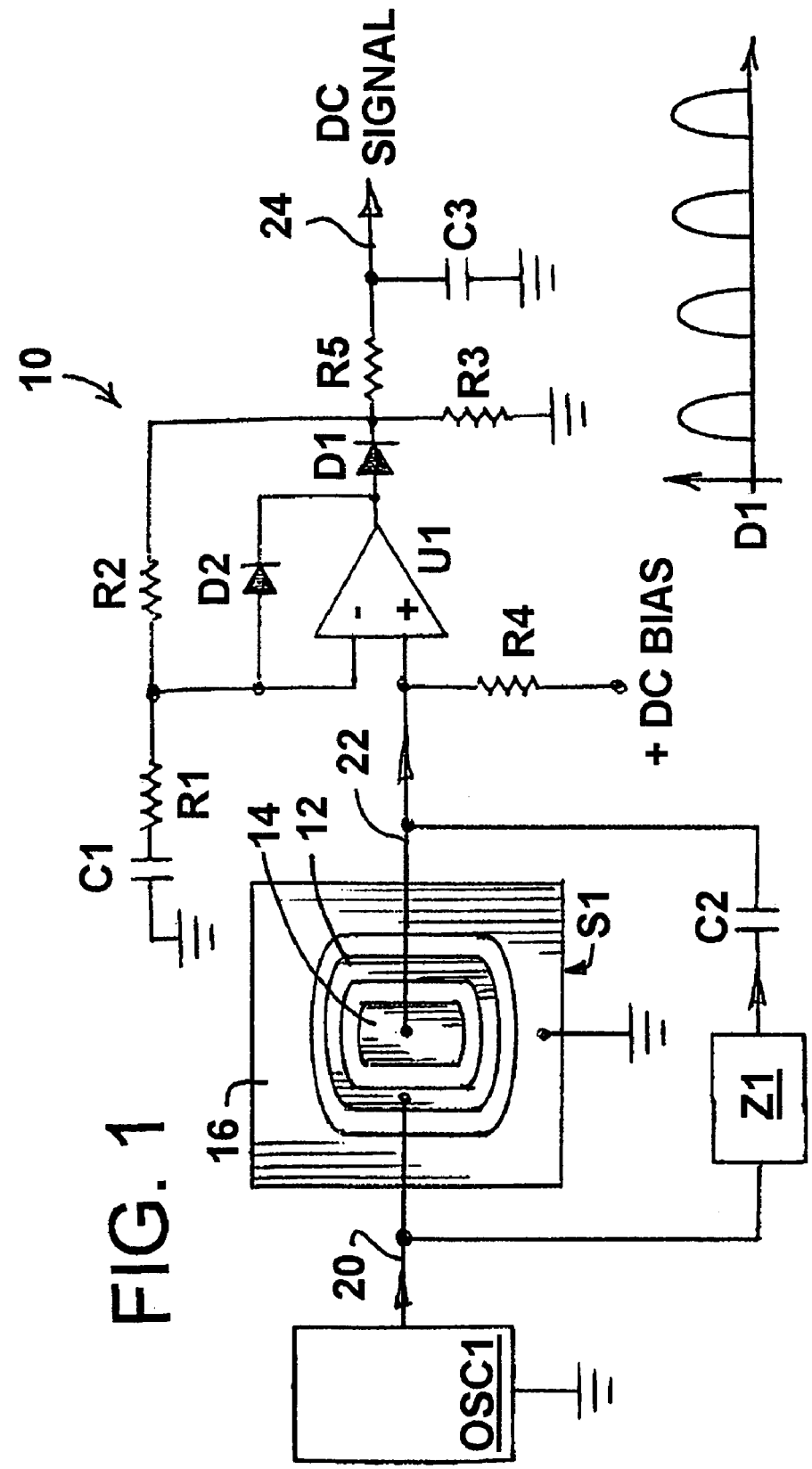
FIG. 1 is a schematic diagram of a circuit for part of a moisture sensing apparatus illustrating a first embodiment of the invention.

Referring now to the drawings, in which like reference numerals are used to refer to the same or similar elements, FIG. 1 illustrates a moisture sensing apparatus comprising an oscillator OSC1 having an output 20 for supplying an AC signal to the driven ring 12 of a contact sensor S1. The sensor S1 also has a sensor pad 14 spaced inwardly of the ring 12 by a first closed loop, and a common ground plane or plate 16, spaced around the ring 12 by a second closed loop.

The circuitry of the apparatus includes an operational amplifier U1 having one (non-inverting) input connected to the pad 14, and another (inverting) input. The amplifier U1 also has an output connected to a first diode D1 with an output of D1 supplying a rectified signal that is proportional to a moisture content of material that is in contact with the sensor S1.

Operational amplifier U1 is not provided with a negative power supply. Instead, ground is used. Therefore, the operational amplifier output cannot swing negative in any event. A second diode D2 would be provided in the circuit to avoid rising of the summing junction by more than one diode voltage drop above ground if a negative supply were provided (i.e., the output potential of the amplifier) when the rectifier input resistor drive swings positive. This prevents rectifier output errors of any significant magnitude from occurring. Diodes D1 and D2 and the resistive and capacitive members shown in FIG. 1 and connected thereto, form a precision rectifier generally designated 10 to be described in greater detail later.

The sensor S1 comprises means, such as an insulating circuit board material or panel, defining a support substrate with the sensor pad 14, the ring 12 and ground plate 16, formed on the support substrate, all lying in a common contact plane for the sensor. The contact plane is preferably flat but may be curved or otherwise three dimensional in shape for special purposes. The contact plane must only be adapted to be in contact with a surface for measuring the moisture content at that surface according to the present invention.

Moisture content at the surface and, to some extent, within the sample, is measured as a function of capacitance across the closed loops between the pad, the ring and the plate. According to the invention, the pad, the ring and the loops having no angular corners so as to minimize electrostatic field fringing effects.

Precision Rectifier:

The present invention primarily addresses means for AC-DC signal conversion such that temperature dependence considerations of diode or other PN junction detectors are eliminated or greatly diminished.

With the advent of low power high frequency operational amplifiers, the practicability of implementing precision rectifier techniques within low cost, low power instruments, has greatly increased. Precision rectifier techniques are known to those skilled in the art, and comprise a means of essentially eliminating diode and PN junction forward voltage effects, including those arising from temperature dependence. A key feature in that regard is incorporation of the diode D1 within a feedback loop, where open loop gain of an operational amplifier in the circuit, diminishes diode non-idealities, virtually completely. While diode capacitances and stored charge considerations yet apply at high frequencies, diodes may be chosen which are substantially free of such considerations below a frequency of 1 MHz. One example is the series of hot-carrier diodes (e.g. the 1N5712) manufactured by Agilent Corporation.

As noted above, FIG. 1 illustrates one embodiment and approach of the present invention.

Sensor S1 contains the ring electrode 12 fed with an AC signal from the output 20 of oscillator OSC1, which oscillator may be of any configuration customarily employed for approximate sine wave generation, e.g. Colpitts or Hartley topology.

The center electrode pad 14 is connected to the non-inverting input of operational amplifier or opamp U1, and to resistor R4 which provides a DC bias to set the quiescent operating point for opamp U1. Signal amplitude at the center pad 14 of sensor S1 is dependent upon the dielectric constant and water content of the sample with which sensor S1 is in contact. As known to those skilled in the art, the dielectric constant of water is more than an order of magnitude greater than that of commonly used construction materials, e.g. wood, concrete and gypsum. Therefore, a relatively small percentage of water content by weight produces a significant sensor center pad voltage signal change due to an increase in capacitive coupling between the ground plane or common plate 16 surrounding the excited ring 12, and the center pad 14 of sensor S1.

An impedance Z1 is connected between the oscillator output 20 connected to the ring electrode 12, and the connection 22 to opamp U1. This impedance provides the center pad 14 of sensor S1 with a sample of the oscillator OSC1 excitation, in order to provide a baseline signal to the detector to establish an AC voltage datum from which the decrease in sensor center pad voltage during sample reading may be established.

Commonly, impedance Z1 is a resistor in the prior art, but the inventor has determined an advantage in the use of a partially reactive component for Z1, which is discussed later in this disclosure.

Amplifier U1, as illustrated in FIG. 1, is used in a non-inverting configuration, although an inverting connection can also be employed. As known to those skilled in the art, the ratio 1+(R2/R1) establishes the gain at frequencies where the reactance of capacitor C1 is very low. Capacitor C1 is employed in order to maintain unity amplifier gain at DC, in order that a non-inverting input DC BIAS, applied through a resistor R4, may be used to accurately define an output voltage swing center point of the amplifier U1. The DC operating point, in conjunction with the gain as just defined, is chosen such that output of the amplifier closely approximates a positive-going half sine, i.e. it serves in practice as an idealized half wave rectifier, with diode D1 included in the feedback loop as described earlier and as schematically illustrated in FIG. 1.

The second diode D2 between the opamp U1 output and its inverting input, conducts on negative going half cycles in the general case where U1 may be operated with both a negative and positive power supply. Resistor R3 at the output of the first diode D1, may be employed to prevent leakage current through diode D1 from causing the cathode of diode D1 to go negative in the event that a ground connection rather than a negative power supply is used for U1. In that context, it is preferable that resistor R3 be substantially lower in value than resistor R2.

Although a half wave rectifier configuration is illustrated in FIG. 1, with the output of diode D1 schematically shown, a full wave precision rectifier configuration as known to those engaged in the art, may also be employed. Further, although FIG. 1 illustrates implementation of voltage measurement at the center pad 14 of sensor S1, current measurement, as in a direct connection to an operational amplifier summing junction, may also be employed.

Output 24 of the thus formed precision rectifier generally designated 10, is averaged to a DC value by a resistor R5 and capacitor C3. The DC average signal represents the area under the half sine output pulses from the rectifier illustrated in FIG. 1.

The DC signal is then routed to a low frequency amplifier (not shown) for scaling, possible zero suppression and meter drive circuitry. It may also be routed to an analog-to-digital convertor (not shown) for use with digital display or data acquisition means.

Figure 2:
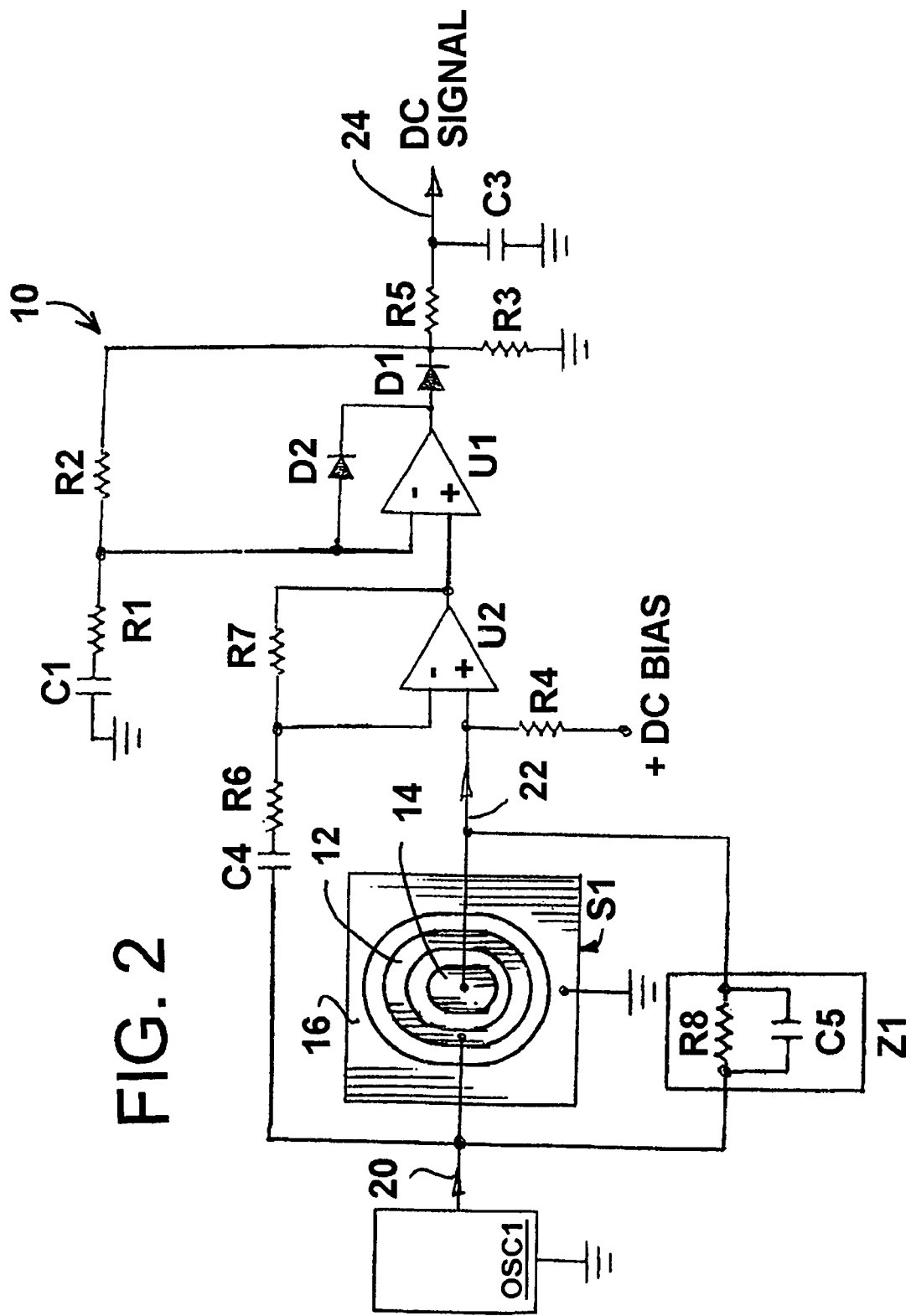
FIG. 2 is a diagram similar to FIG. 1 of a second embodiment of the invention.

Differential Amplifier:

A modification to the circuitry of FIG. 1 is illustrated in FIG. 2.

Since the AC amplitude at the center receiving pad 14 of sensor S1 is a relatively high non-zero value, when no sample is present at the sensor, a differential amplifier may be used ahead of the precision rectifier circuit 10 to cancel or "buck out" a significant part of the center pad signal by using a sample of the sensor excitation signal.

In that manner, moisture content readings may be more accurate than with employment of the precision rectifier 10 alone, due to substantial elimination of the baseline center pad signal of S1 by use of the very signal, i.e., the oscillator output which produces the baseline signal in the first place.

Differential amplifier (amp) U2 in FIG. 2 may be configured with unequal gains for each input. In the instant shown, gain at the non-inverting input is higher than that at the inverting input due to the influence of resistors R6 and R7. Capacitor C4 serves as a DC block and for introduction of the oscillator signal for partial cancellation of the sensor center pad signal when no moisture sample is present at the sensor S1.

Values of R6 and R7 may be chosen to alter the cancellation extent, as the gain of amp U2 for cancellation is simply −(R7/R6), whereas gain of amp U2 from the standpoint of the sensor center pad 14 is 1+(R7/R6) as stated earlier.

Sensor Coupling Impedance Z1:

In some extant capacitance moisture meter designs, impedance Z1 is comprised of a resistor or resistive member, such as a resistor R6 shown in FIG. 2 of U.S. Pat. No. 5,486,815. The present inventor has determined that use of a parallel resistor-capacitor pair is advantageous in increasing dynamic range of the differential amplifier while maintaining the same nominal value of gain as established by resistors R6 and R7 in FIG. 2 of the present disclosure.

Without the capacitive component or member (C5), a degree of phase shift exists between the sensor center pad signal (i.e. non-inverting input to U2) and sensor ring excitation (i.e. output 22 of the oscillator OSC1) when a sensor sample is not present.

This is due to stray capacitances at the amplifier non-inverting input, printed circuit board conductors, and the relatively loose capacitive coupling between the driven sensor ring 12 and the center pad 14 of the sensor. The subject phase shift is also a function of a resistive-only component of impedance Z1, the only non-reactive component in what otherwise would be a totally reactive (capacitive) path from the oscillator to the non-inverting input of U2. The phase shift prevents signal cancellation at the output of amp U2 from being as perfect as possible if phase shift were not present.

When a moisture measurement sample is present at the sensor S1, increased capacitive coupling is present between the sensor center pad 14 and both the driven ring 12 and ground plane or plate 16 of the sensor. The phase change introduced by the increased coupling effectively provides capacitive swamping of the resistive part, i.e. resistor R8 of impedance Z1, and allows phases of the non-inverting and inverting inputs of amp U2 to more closely approach each other. When only resistor R8 is present under no-sample conditions, the phase shift described above limits the degree of cancellation possible by the differential amplifier U2, and thus decreases dynamic range of the same during sensing of samples with widely varying moisture content.

Introduction of capacitor C5, the capacitive component of Z1, decreases phase shift of the inputs to U2 under no-sample conditions, thereby increasing dynamic range of the differential amplifier.

Sensor Geometry:

Many prior art moisture meter designs are based upon co-planar sensors, utilize sensor patterns that are rectangular in nature. Such is the case, for example, regarding the sensor explicitly described in U.S. Pat. No. 5,486,815.

The present inventor has determined the optimum sensor center pad and driven ring geometry to be other than rectangular, i.e. circular, elliptical, round-cornered, race-track shaped, or oval. The stated observation has occurred during tests of various sensor geometries with the electronic circuitry of the invention.

Greater sensitivity has been obtained, for example, with an oval sensor than with a rectangular sensor with angular corners, where center pad 14 (receiving electrode) areas are identical. It is believed that by eliminating sharp angular corners in the sensor areas, electrostatic field fringing effects at the corners of a rectangular or square sensor are eliminated, where coupling of the center pad receiving electrode to the outer ground plane 16 through the dielectric of the sample under test was compromised. This observation is further supported by testing of rectangular sensors with small scale interdigitated or serpentine patterns, where sensitivity was found to decrease as compared with an ordinary rectangular sensor.

Figure 3:
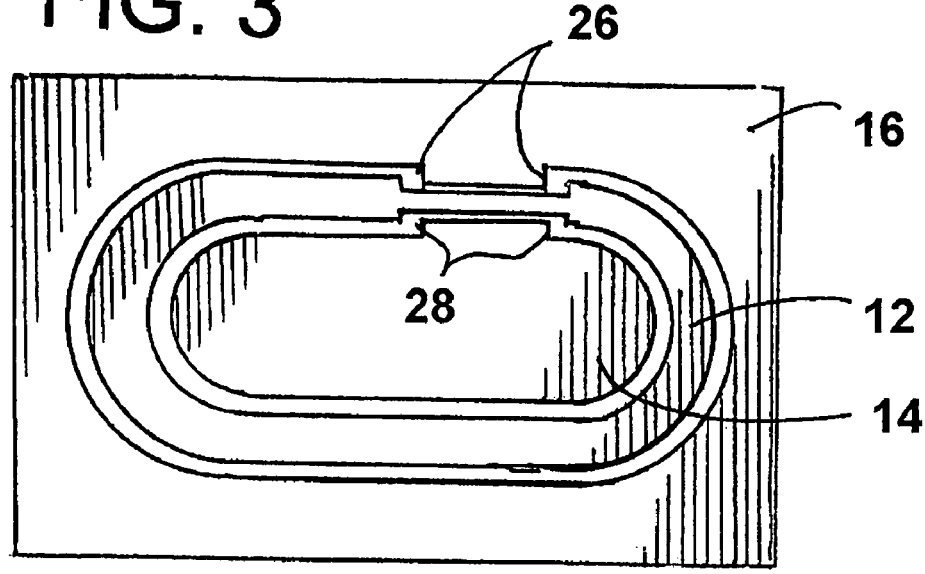
FIG. 3 is a plan view of an embodiment of a contact sensor of the present invention.

A typical oval sensor is shown in FIG. 3. The necked area in the transmitting (ring) electrode is intended for connector installation by soldering to the copper foil on printed circuit board material used as the sensor substrate.

Figure 4:
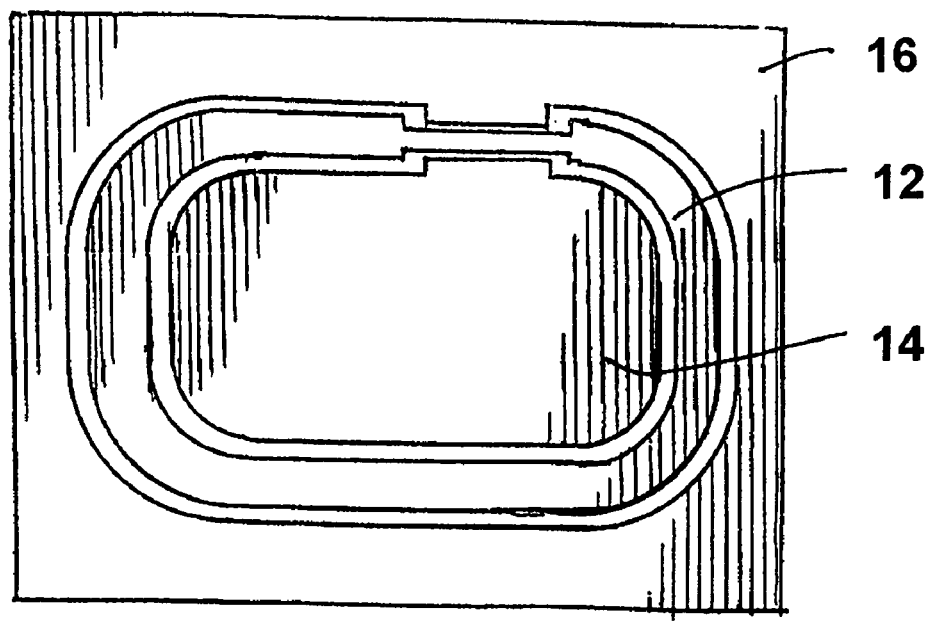
FIG. 4 is a view similar to FIG. 3 of another embodiment of the contact sensor of the present invention.

FIGS. 1 and 2 illustrates other round-cornered shapes for the pad and ring, as does FIG. 4.

For this disclosure the word "oval" is used to mean elliptical (a mathematically defined shape having two spaced apart foci), circular (a class of ellipse where the two foci are merged into a single center of curvature) or any other oblong, rounded egg or similar shape that may or may not have a strict mathematical definition. Race-track shaped is meant to convey any generally polygonal shape with non-angular, rounded corners. A rectangle with rounded corners is also possible for the sensor of the invention, including the special case of a square where all sides have equal length. The non-angular corners of the invention should have a radius of curvature of at least about 1/16 inch or about 2 mm, and preferably at least about 1/4 inch or about 6 mm.

While specific embodiments of the invention has been shown and described in detail to illustrate the application of the principles of the invention, it will be understood that the invention may be embodied otherwise without departing from such principles.

What is claimed is:

1. A moisture sensing apparatus, comprising:
   an oscillator having an output for supplying an AC signal;
   a sensor having a sensor pad, a driven ring around the pad and connected to the oscillator output, and a ground plate around the ring; and
   a precision rectifier connected to the sensor for rectifying a signal from the sensor to form a DC signal that is proportional to the moisture content, the precision rectifier comprising:
   an operational amplifier having one input connected to the pad, another input, and an output, the operational amplifier being operative to obtain a difference between input signals;
   a first diode connected to the output of the operational amplifier and in a feedback loop between the operational amplifier output and the other input of the operational amplifier to nullify variations in the rectified signal that are due to temperature induced variations of diode parameters, the first diode having an output for supplying a rectified signal that is a monotonic function of moisture content of material that is in contact with the sensor; and
   a second diode connected between the output and the other input of the operational amplifier for reducing output errors.

2. The moisture sensing apparatus of claim 1, including a reactive impedance connected across the pad and ring of the sensor for providing a baseline signal for the rectified signal.

3. The moisture sensing apparatus of claim 2, wherein the reactive impedance comprises parallel connected, resistance and capacitance members.

4. The moisture sensing apparatus of claim 1, including a differential amplified circuit connected between the operational amplifier and the sensor for cancelling part of a signal from the pad of the sensor, using a sample of AC signal from the oscillator.

5. The moisture sensing apparatus of claim 1, wherein the sensor comprises means defining an support substrate, the sensor pad being on the support substrate, the driven ring being on the support substrate and extending around the pad and spaced from the pad to define a first closed loop around the pad, and the ground plate being on the support substrate and extending around the ring and defining a second closed loop around the ring, the pad, the ring and the plate all lying in a common contact plane for the sensor, which contact plane is adapted to be in contact with a surface for measuring moisture content at the surface as a function of capacitance across the loops, the pad, the ring, the plate, and the loops having no angular corners so as to avoid electrostatic field fringing effects.

6. A contact sensor for a moisture sensing apparatus having an oscillator with an output for supplying an AC signal and an operational amplifier with precision rectifier means for supplying a rectified signal that is proportional to a moisture content of material that is in contact with a contact plane of the contact sensor, the contact sensor, comprising:
   means defining an support substrate;
   a conductive sensor pad on the support substrate;
   a conductive driven ring on the support substrate, extending around the pad and spaced from the pad to define a first closed loop around the pad; and
   a conductive ground plate on the support substrate, extending around the ring and defining a second closed loop around the ring;
   the pad, the ring and the plate all lying in the contact plane for the sensor, which contact plane is adapted to be in contact with a surface for measuring moisture content at the surface, as a function of capacitance across the loops;
   the pad, the ring, the plate, and the loops having no angular corners to avoid electrostatic field fringing effects, wherein
   the precision rectifier means comprises:
   an operational amplifier having one input connected to the pad, another input, and an output;
   a first diode connected to the output of the operational amplifier and in a feedback loop between the operational amplifier output and the other input of the operational amplifier to nullify variations in the rectified signal that are due to temperature induced variations of diode parameters, the first diode having an output for supplying a rectified signal that is a monotonic function of moisture content of material that is in contact with the sensor; and
   a second diode connected between the output and the other input of the operational amplifier for reducing output errors, and
   the operational amplifier being operative to obtain a difference between input signals.

7. The contact sensor of claim 6, wherein at least one of the loops is oval.

8. The contact sensor of claim 6, wherein at least one of the loops is rectangular with rounded corners.

9. The contact sensor of claim 6, wherein at least one of the loops is racetrack shaped.

10. The contact sensor of claim 6, wherein all corners of the pad, the ring, the plate, and the loops have radii of at least 1/16th inch.

11. A moisture sensing apparatus comprising:
    an oscillator having an output for supplying an AC signal;
    a contact sensor connected to the oscillator for changing the AC signal as a function of moisture content at a surface in contact with the contact sensor;
    a precision rectifier connected to the sensor for rectifying a signal from the sensor to form a DC signal that is proportional the moisture content; and
    a reactive impedance connected across the sensor for providing a baseline signal for DC signal, wherein
    the precision rectifier comprises:
    an operational amplifier having one input connected to the sensor, another input, and an output;
    a first diode connected to the output of the operational amplifier and in a feedback loop between the operational amplifier output and the other input of the operational amplifier to nullify variations in the rectified signal that are due to temperature induced variations of diode parameters, the first diode having an output for supplying a rectified signal that is a monotonic function of moisture content of material that is in contact with the sensor; and a second diode connected between the output and the other input of the operational amplifier for reducing output errors, and the operational amplifier being operative to obtain a difference between input signals.

12. The moisture sensing apparatus of claim 11, wherein the reactive impedance comprises parallel connected, resistance and capacitance members.

13. The moisture sensing apparatus of claim 11, wherein the sensor has a cental pad with no angular corners.

14. The moisture sensing apparatus of claim 11, wherein the precision rectifier comprises an operational amplifier having one input connected to a pad of the sensor, the operational amplifier having another input, and an output, a first diode connected to the output of the operational amplifier and in a feedback loop between the operational amplifier output and the other input of the operational amplifier to nullify variations in the DC signal that arise from temperature induced variations in diode parameters, the first diode having an output for supplying the DC signal, and a second diode connected between the operational amplifier output and the other input of the operational amplifier.

15. The moisture sensing apparatus of claim 14, including a differential amplified circuit connected between the operational amplifier and the sensor for cancelling part of a signal from the pad of the sensor, using a sample of AC signal from the oscillator.

\* \* \* \* \*